United States Patent [19]

Alexander et al.

[11] Patent Number: 4,981,844
[45] Date of Patent: Jan. 1, 1991

[54] METHOD TO IMPROVE IMMUNE RESPONSE AND RESISTANCE TO INFECTION FOLLOWING SURGERY BY DIET COMPOSITION

[75] Inventors: J. Wesley Alexander; Michael D. Peck, both of Cincinnati, Ohio

[73] Assignee: University of Cincinnati, Cincinnati, Ohio

[21] Appl. No.: 253,140

[22] Filed: Oct. 4, 1988

[51] Int. Cl.⁵ .................... A61K 31/20; A61K 31/355
[52] U.S. Cl. .................................... 514/21; 514/549; 514/552; 514/560; 514/2
[58] Field of Search .......................... 514/21, 549, 560

[56] References Cited

U.S. PATENT DOCUMENTS

| 4,101,673 | 7/1978 | Chang | 514/549 |
| 4,474,773 | 10/1984 | Shinitzky et al. | 514/78 |
| 4,752,618 | 6/1988 | Mascioli et al. | 514/549 |

OTHER PUBLICATIONS

Thomas et al. J. Nutr. 115:1528–1534, 1985.
Mascioli et al. Am. J. Clin. Nutr. 1989. 49:277–82.
Yoshikawa et al: Mie Med. Journ., vol. XXXV, No. 1, issued 1985 pp. 95–100, "Resistance to Opportunistic Infections . . ."
Dayton et al: J. Nutr., vol. 107, issued 1977, pp. 1353–1360, "Effect of High-Oleic and High-Linoleic Safflower Oils . . ."
Alexander et al. Annals of Surgery Jul. 1986, vol. 204, No. 1, pp. 1–8.

Primary Examiner—Howard E. Schain
Assistant Examiner—Choon P. Koh
Attorney, Agent, or Firm—Wood, Herron & Evans

[57] ABSTRACT

The immune response of a patient can be improved pre-operatively by altering the diet of a patient. When 20 to about 80% of the calories in a diet are from linoleic acid which is an omega 6 fatty acid, the immune response system and resistance to infection of the patient is substantially improved. Likewise providing 100 to about 1,000 IU per day of vitamin E in the diet also improves the immune response of the patient pre-operatively. This in turn improves the survival rate of the patient.

3 Claims, No Drawings

METHOD TO IMPROVE IMMUNE RESPONSE AND RESISTANCE TO INFECTION FOLLOWING SURGERY BY DIET COMPOSITION

BACKGROUND OF THE INVENTION

Surgical procedures can act to seriously weaken the body of the patient. Major surgeries are in fact an extreme assault upon the body which in turn affects the immune response system of the patient. This in turn increases the risk of post-operative infection. Such post-operative infection has a significant effect upon the survival rate after major surgery.

Further many patients prior to surgery are already in a particularly debilitated condition. Many patients who have digestive track problems which require surgery have not been able to ingest sufficient calories to maintain body weight and keep themselves in a healthy condition. Accordingly, many patients require a pre-operative stay to obtain either an enteral or parenteral diet to increase body weight and improve their health.

It has been shown that diet can affect the immune response system after major assaults to the body. For example, The Importance of Lipid Type in the Diet After Burn, *Anals. of Surgery*, Vol. 204, No. July, 1, 1986 reports that the lipids contained in a diet have an effect on the immune response system in burn patients. Specifically, it indicated that a diet high in omega 6 fatty acids such as linoleic acid have a significant immunosupressive effect. On the other hand, diets high in omega 3 fatty acids improve the immune response. In "The Effect of Dietary Unsaturated Fatty Acids and Indomethacin on Metabolism and Survival after Burn" indicates that excessive dietary polyunsaturated linoleic acid may influence immunocompetence after burn. Accordingly, all indications are that omego 6 fatty acids have a immunosuppressive effect.

SUMMARY OF THE INVENTION

The present invention is premised on the realization that prior to an operative procedure the immune response system of a patient can be improved by providing the patient with a diet very high in linoleic acid. More particularly the present invention is premised on the realization that a diet having from about 20 to about 60% of its total calories derived from linoleic acid substantially improves the immune response system of patients and acts as a preoperative diet to enhance the survival rate following major operative procedures.

Further the present invention is premised on the realization that a diet high in vitamin E has a similar effect on the immune response system. In combination a diet high in vitamin E as well as a diet high in linoleic acid provides a significant improvement in the immune response systems of patients prior to operative procedures.

Other objects and advantages of the present invention will be appreciated in light of the following detailed description.

DETAILED DESCRIPTION OF THE INVENTION

In order to improve the immune response system of surgical patients, the patient is provided a diet which is high in the omega 6 fatty acid linoleic acid and further is provided with a diet which is high in vitamin E. By ingesting the diet prior to operative procedures the resistance to infection by the patient is significantly improved.

For purposes of the present invention, major operative procedures would include any operative procedure requiring general anethesia that has a risk of infection including patients suffering from malnutrition. Basically the resistance to infection of a patient prior to any operative procedure could be improved by the present invention.

The diet for use in the present invention will include a source of protein, a source of carbohydrate, and a source of fats, i.e., fatty acids. In addition to these compositions the diet will include vitamin and mineral supplement.

The diet which can be either designed to be a parenteral diet or an enteral diet depending on the patient will be generally an aqueous mixture of protein (amino acid), carbohydrate and fat along with vitamin and mineral sources. The total calories in the diet which should be ingested by the patient will be from about 20 to about 60 kilocalories per kilogram body weight per day. The total energy needs vary according to the individual. Generally acceptable limits are well known and are set forth by the National Research Counsel in the Recommended Daily Allowance.

The total calories of the diet will be derived from the carbohydrates, the protein and the fats. Generally it is desirable that from about 12 to about 25% of the total calories be provided by the protein. For an enteral diet suitable sources of protein would include milk proteins, soy protein and others. It is also preferable to include 1-2% arginine. For a parenteral diet a combination of amino acids should be employed instead of the protein. These can include leucine, lysine, valine, isoleucine, phenylalanine, threonine, methionine, histidinine, tryptophan. These are considered the essential amino acids. Other non-essential amino acids can include glutamic acid, proline, aspartic acid, serine, arginine, alanine, glycine, glutamine and tyrosine. These are considered the non-essential amino acids. These would be provided generally in a total parenal nutrition diet.

Further from about 10 to 70% of the total calories of the diet should be provided by the carbohydrate source. A wide variety of simple sugars can be used as a source of carbohydrates such as for example dextrose, fructose, sucrose and the like in combinations. Enteral diets should include complex carbohydrates such as corn starch and dextrins.

From about 20 to about 80% of the total calories of the diet should be derived from lipids. Generally 20 to 60% of the diet calories will be derived from lipid. From about 50 to about 100% and generally 50-70% of the calories of these lipids should be derived from linoleic acid. A major source of linoleic acid is safflower oil which contains from about 70 to about 85% linoleic acid. However, linoleic acid can be purchased and used.

In addition to the protein, carbohydrate and fatty acid the diet should include a source of vitamins as well as minerals. In particular the present invention should be relatively high in vitamin E. The diet should include about 100 to about 1,000 IU per day of vitamin E. Generally the amount of vitamin E will be about 100 to 300 IU per day until the day immediately prior to surgery when the amount of vitamin E should be increased to about 1,000 IU per day. In addition to vitamin E the diet of the present invention should include 5,000-10,000 IU micrograms retinol equivalents vitamin A per day, 400 IU per day of vitamin D, 1-5 grams per day of vitamin C, 0.4 milligrams of folic acid, 20 milligrams per day of niacin, 2 milligrams per day of riboflavin, 1.5 milligrams per day of thiamine, 2 milligrams per day of vitamin B6, 3 micrograms per day of vitamin B12, 1.5 grams per day of calcium, 1.5 grams per day of phosphorous, 150 micrograms per day of iodine, 10 milligrams per day of iron and 400 milligrams per day of magnesium. With the exception of the vitamin E the above components can be varied widely and/or eliminated without departing from the present invention.

An exemplary enteral formulation of the present invention will include the following:

| | |
|---|---|
| Whey protein | 20% total calories |
| Safflower oil | 50% total calories |
| Dextrins | 30% total calories |
| Vitamin A | 5,000 micrograms retinol equivalents/liter |
| Vitamin D | 200 IU/l |
| Vitamin E | 50 IU/l |
| Vitamin C | 2 gms/l |
| Folic Acid | 200 micrograms/liter |
| Niacin | 10 mg/l |
| Riboflavin | 1 mg/l |
| Thiamine | 750 micrograms/liter |
| Vitamin B6 | 1 mg/l |
| Vitamin B12 | 1.5 micrograms/liter |
| Calcium | 750 mg/l |
| Phosphorous | 750 mg/l |
| Iodine | 75 micrograms/liter |
| Iron | 5 mg/liter |
| Magnesium | 200 mg/liter |

This diet has a caloric content of 1 calorie per ml.

The diet of the present invention is administered to a patient for a time effective to improve the immune response of the patient. Generally it is administered for 14 days prior to the operative procedure. The diet should be administered to the patient at least 10 days prior to the operative procedure. This can be increased up to six weeks depending upon the need of the patient and the state of debilitation. In the event a weight gain is necessary prior to the operative procedure the diet can be administered and ingested by the patient for whatever period of time necessary to develop the weight gain.

With respect to the vitamin E this can be excluded from the diet although it provides substantial beneficial results and should be provided at about 100 to 300 IU per day. On the day immediately prior to surgery the diet should be supplemented with additional vitamin E up to 1,000 IU per day in order to further improve the immune response system.

In order to test the efficacy of the present invention animal models were employed. In order to simulate the effect of major surgery the test animals were fed various diets and then subjected to a burn as indicated below. They were then infected with Pseudomonas aeruginosa. The survival rate of the mice after two weeks then provided an indication of the effect of diet on the immune system.

EXAMPLE

Female albino inbred (Balb/c) mice were obtained from Charles River Suppliers and allowed to acclimate in laboratory facilities for one week. They were housed five in a cage in a room with twelve hour alternating light and dark cycles and given water and natural chow (Wayne Rodent Blox) ad libitum. The animals were then weighed and begun on experimental diets ad libitum. The mice were fed several different diets prior to the burn. The natural diet is composed of soybean meal, fishmeal, corn and wheat and by weight contains 24% protein, 4% fat, and 4.5% fiber. A purified diet was formed by weight containing 20% protein as casein, 65% carbohydrate as sucrose and corn starch, 5% fat as corn oil, 5% fiber as purified cellulose and vitamins and minerals. The purified diet was then modified by substituting other fat sources and for a high fat diet, increasing the fat content. When the amount of fat was increased to 20% a weighted reduction in sucrose and corn starch was made. Thus the low fat diets contained 5% by weight fat which was 12% of the total calories and 15% of non-protein calories. The high fat diets contain 20% fat by weight which is 40% of the total calories and 50% of the non-protein calories.

The fatty acid compositions of the fat sources were determined with gas liquid chromatography. The oils, coconut oil, corn oil, oleic acid and safflower oil were all of food grade and obtained from ICN Biochemicals. The MaxEPA oil was donated by R. P. Ssherer Corporation.

Chromatographic analysis of the fats used in the diets yielded the following results. The fatty acid composition of the corn oil was 45% myristic acid, 31% linoleic acid and 23% palmitic acid. Composition of corn oil used in the purified control diet was 50% linoleic acid, 29% oleic acid and 16% palmitic acid. The composition of the MaxEPA oil was 28% palmitic acid, 18% oleic acid and 18% eicosapentaenoic acid, 15% docosahexaenoic acid and 4% linoleic acid. The total omega 3 content of MaxEPA was thus 37%. The fatty acid composition of natural chow used for control was 47% linoleic acid, 24% oleic acid and 17% palmitic acid and 5% linoleic acid. The composition of the food grade oleic acids in the diets was 78% oleic acid, 14% palmitic acid, 4% linoleic acid and 4% myristic acid. The composition of the safflower oil was 91% linoleic acid, 8% palmitic acid (which represents a higher amount of linoleic acid than was commonly found in safflower oil usual range 70-80%).

At the end of two weeks they were again weighed and the fur was clipped from their back. General anesthesia was obtained with methoxyfluorane and a 1.5 inch by 2 inch Teflon template was applied to the dorsum of the animal. The exposed area was saturated with 95% ethanol and ignited for 12 seconds. The animal was then fluid resuscitated with 1 ml PBS. Sixteen to eighteen hours after burning $2.5 \times 10^5$ viable Pseudomonas aeruginosa were injected subeschar. Mortality was noted over the next week and the survivors were sacrificed with $CO_2$ euthanasia. The first experiment compared the natural control diet to the purified high fat diets, i.e., the diet with high safflower oil content (20% by weight) and the high MaxEPA fat content (20% by weight). The second experiment compared the natural control diet to the purified low fat diets, i.e., the low safflower oil diet (5% by weight) and the low MaxEPA oil diet (5% by weight). The third experiment compared the purified control diet to the purified high fat diets. The fourth experiment compared four high fat diets using coconut oil, MaxEPA, oleic acid and safflower oil all at 20% by weight.

The survival rate of the mice and their respective diet are listed in Table I.

TABLE I

| Experiment 1 | |
|---|---|
| Natural Chow | 33% |
| MaxEPA (20%) | 40% |

TABLE I-continued

| | |
|---|---|
| Safflower Oil (20%) | 67% |
| Experiment 2 | |
| Natural Chow | 41% |
| MaxEPA (5%) | 39% |
| Safflower Oil (5%) | 47% |
| Experiment 3 | |
| Purified Diet | 44% |
| MaxEPA (20%) | 18% |
| Safflower Oil (20%) | 54% |
| Experiment 4 | |
| Safflower Oil (20%) | 87% |
| Oleic Acid (20%) | 53% |
| Coconut Oil (20%) | 55% |
| MaxEPA (20%) | 30% |

In a related experiment Balb/c mice were subjected to a 20% total body surface area third degree flame burn under general anesthesia and resuscitated. Viable Pseudomonas aeruginosa were injected subeschar the next day. Three groups were tested. Vitamin E was given by Gavage in doses of 2.5 IU, 25 IU and 250 IU on four consecutive days, the two days before burn the day of burn and the day of infection. Survival was improved in the 25 and 250 IU/kg groups compared to control. Vitamin E was then given by Gavage on day 0, day 1 or day 2 in three doses. Mortality in the 2.5 and 25 IU groups on day 1 was worse than control or high dose. Accordingly, providing vitamin E given at least 25 IU (greater than 10 times the RDA for mice) by Gavage prior to injury and continued thereafter for two days does improve survival. The benefit is not seen if vitamin E is not started prior to injury.

This accordingly provides a very useful pre-operative diet including both a high concentration of linoleic acid and a high (greater than 10 times RDA) vitamin E content. A patient's ingesting this diet prior to operative procedures will substantially reduce the likelihood of developing an infection.

The preceding has been a description of the preferred embodiment of the present invention as well as the best mode of the invention currently known. However, the invention is to be defined only by the appended claims wherein we claim:

We claim:

1. A method of improving the immune response in patients comprising:
    said patient ingesting a diet for at least 10 days prior to an operative procedure, said diet having 20–60 kilocalories per kilogram body weight wherein 20% to 80% of the calories in said diet are derived from linoleic acid.

2. The method claimed in claim 1 wherein said diet includes 100 to 1,000 IU per day vitamin E.

3. The method claimed in claim 1 wherein said diet contains from about 20 to about 60% safflower oil.

* * * * *

UNITED STATES PATENT AND TRADEMARK OFFICE
CERTIFICATE OF CORRECTION

PATENT NO. : 4,981,844

DATED : January 1, 1991

INVENTOR(S) : J. Wesley Alexander etal

It is certified that error appears in the above-identified patent and that said Letters Patent is hereby corrected as shown below:

Please add the following at Column 1, line 5

"This invention was made with Government support under AI-12936 awarded by the National Institute of Health, The Government has certain rights in the invention."

Signed and Sealed this

Eighth Day of December, 1992

Attest:

DOUGLAS B. COMER

Attesting Officer

Acting Commissioner of Patents and Trademarks